(12) United States Patent
Pau et al.

(10) Patent No.: US 7,391,936 B2
(45) Date of Patent: Jun. 24, 2008

(54) MICROFLUIDIC SENSORS AND METHODS FOR MAKING THE SAME

(75) Inventors: Stanley Pau, Hoboken, NJ (US); Mark P. Earnshaw, Morristown, NJ (US)

(73) Assignee: Lucent Technologies, Inc., Murray Hill, NJ (US)

( * ) Notice: Subject to any disclaimer, the term of this patent is extended or adjusted under 35 U.S.C. 154(b) by 0 days.

(21) Appl. No.: 11/040,269

(22) Filed: Jan. 21, 2005

(65) Prior Publication Data

US 2006/0165342 A1    Jul. 27, 2006

(51) Int. Cl.
   G02B 6/00   (2006.01)
   G01N 21/05  (2006.01)

(52) U.S. Cl. .............................. 385/12; 385/14; 385/27; 385/39

(58) Field of Classification Search .................. 385/12, 385/33, 13
   See application file for complete search history.

(56) References Cited

U.S. PATENT DOCUMENTS

| | | | |
|---|---|---|---|
| 4,553,243 A | 11/1985 | Rosenwaks et al. | 372/89 |
| 4,653,062 A | 3/1987 | Davis et al. | 372/89 |
| 4,688,893 A | 8/1987 | Laakmann | 350/96.32 |
| 5,165,005 A | 11/1992 | Klainer et al. | 385/129 |
| 5,378,449 A | 1/1995 | Dinges | 423/579 |
| 5,589,136 A | 12/1996 | Northrup et al. | 422/102 |
| 5,595,712 A | 1/1997 | Harbster et al. | 422/129 |
| 5,846,842 A | 12/1998 | Herron et al. | 436/518 |
| 5,870,422 A | 2/1999 | Florentino et al. | 372/89 |
| 5,876,675 A | 3/1999 | Kennedy | 422/99 |
| 5,922,591 A | 7/1999 | Anderson et al. | 435/287.2 |
| 5,974,072 A | 10/1999 | Hartlove et al. | 372/89 |
| 6,099,805 A | 8/2000 | Hartlove | 422/122 |
| 6,154,478 A | 11/2000 | Vetrovec | 372/89 |
| 6,221,226 B1 | 4/2001 | Kopf-Sill | 204/602 |
| 6,224,786 B1 | 5/2001 | Stelman | 252/183.14 |
| 6,248,539 B1 | 6/2001 | Ghadiri et al. | 435/7.1 |
| 6,352,838 B1 | 3/2002 | Krulevitch et al. | 435/34 |

(Continued)

FOREIGN PATENT DOCUMENTS

EP    0 599 248 A1    6/1994

(Continued)

OTHER PUBLICATIONS

Friis et al., Monolithic integration of microfluidic channels and optical waveguides in silica on silicon, Applied Optics, vol. 40, No. 34, pp. 6246-6251 (Dec. 1, 2001).

(Continued)

*Primary Examiner*—Tina M Wong

(57) ABSTRACT

Microfluidic optical sensor comprising: an optical waveguide capable of propagating light from an optical input port to an optical output port, the optical waveguide comprising an optical waveguide interaction region; a fluidic channel capable of conducting a fluid from a fluid input port to a fluid output port, the fluidic channel comprising a fluidic channel region; the fluidic channel region being separated from the optical waveguide interaction region by an interposed spacing material configured to transmit an evanescent field of the light through the spacing material between the optical waveguide interaction region and the fluidic channel region. Microfluidic optical sensor comprising an optical resonator. Methods for making microfluidic optical sensors.

21 Claims, 9 Drawing Sheets

U.S. PATENT DOCUMENTS

| | | | |
|---|---|---|---|
| 6,377,600 B1 | 4/2002 | Flegal | 372/89 |
| 6,438,279 B1 | 8/2002 | Craighead et al. | 385/12 |
| 6,915,028 B2* | 7/2005 | Lyons | 385/12 |
| 6,974,673 B2 | 12/2005 | Lockhart | 435/7 |
| 2002/0181837 A1 | 12/2002 | Wang et al. | 385/16 |
| 2003/0020915 A1 | 1/2003 | Schueller et al. | 356/436 |
| 2005/0186565 A1* | 8/2005 | Malak | 435/5 |
| 2005/0279354 A1* | 12/2005 | Deutsch et al. | 128/200.24 |

FOREIGN PATENT DOCUMENTS

| | | |
|---|---|---|
| EP | 0 891 022 A1 | 1/1999 |
| EP | 0 891 025 A2 | 1/1999 |
| EP | 0 893 704 A2 | 1/1999 |
| EP | 1 059 709 A2 | 12/2000 |
| WO | WO 80/00922 | 5/1980 |
| WO | WO 90/07810 | 7/1990 |
| WO | WO 90/08414 | 7/1990 |
| WO | WO 97/00726 | 1/1997 |
| WO | WO 97/01087 * | 1/1997 |

OTHER PUBLICATIONS

Verpoorte et al., Microfluidics Meets MEMS, Proceedings of the IEEE, vol. 91, No. 6, pp. 930-953 (Jun. 2003).

U.S. Appl. No. 10/444,578, filed May 23, 2003, Pau et al.

U.S. Appl. No. 11/148,549, filed Jun. 9, 2005, Pau et al.

Harendt et al., "Silicon fusion bonding and its characterization," J. Micromech. Microeng., vol. 2, pp. 113-116 (1992).

Wei et al., Low temperature wafer anodic bonding J. Micromech. Microeng., vol. 13, pp. 217-222 (2003).

Luciferin, D., "*Luminescence Analysis*," Biothema, published by (www.biothema.com/luminescenceanalysis), p. 1 (Sep. 2002).

Online publication titled: "*An Introduction to Chemiluminescence and Bioluminescence Measurements*," by "Communication Technology"—(www.comm-tec.com/library/ctd/chemiluminescenceandbioluminesance measurements), pp. 1-11 (dated prior to Apr. 8, 2003.

Wako, Tecan, Application Note: "*Performance of a typical luminescence application demonstrated on two examples of Firefly Luciferase Assays*," (Firefly Luciferase Assay, Doc. No. 391 551), pp. 1-4 (Nov. 2000).

Wood et al., "Complementary DNA Coding Click Beetle Luciferases Can Elicit Bioluminescence of Difference Colors," Science, vol. 244, pp. 700-702 (May 1989).

Cool et al., "*DF-$CO_2$ and HF-$CO_2$ Continuous-Wave Chemical Lasers*," Applied Physics Letters, vol. 15, No. 10, pp. 318-320 (Nov. 15, 1969).

White et al., "*Chemi-and Bioluminescence of Firefly Luciferin*," Journal of the American Chemical Society, pp. 3199-3208 (Apr. 23, 1980).

"*Reactions of Alkanes*," Chemical Reactivity, http://cem.msu.edu/-reusch/VirtualText/funerx1.htm, pp. 1-4 (Apr. 23, 2003).

Gomi et al., "*Oxyluciferin, a Luminescence Product of Firefly Luciferase, Is Enzymatically Regenerated into Luciferin*," The Journal of Biological Chemistry, vol. 276, No. 39, pp. 36508-36513 (Issue of Sep. 28, 2001).

* cited by examiner

MICROFLUIDIC SENSORS AND METHODS FOR MAKING THE SAME

FIELD OF THE INVENTION

The present invention relates to the field of microfluidic sensors and to methods for making such sensors.

BACKGROUND OF THE INVENTION

Microfluidic sensors have been fabricated in order to optically analyze small samples of fluids. For example, sensors have been made comprising a cuvette having optically neutral walls in which a small sample of a fluid to be analyzed is placed, and then a light beam is directed through the cuvette so that properties of the fluid such as the optical refraction, absorption and transmission characteristics can be detected by analysis of the transmitted and emitted light. Since the cuvettes are relatively small in order to place a small fluid sample in position for passage therethrough of a light beam, the path length of the light beam through the fluid in the cuvette is short. Moreover, the diameter of the light beam is generally small, so that the interaction cross-section between the fluid and the light beam also is accordingly small. Hence, in order to obtain a sufficiently strong signal for analysis, such systems typically cause the light beam to make a series of passes through the cuvette before the beam is directed into instrumentation for detecting refraction, absorption and transmission. Such systems are necessarily complex, and may therefore be both cumbersome and delicate. Further microfluidic sensors have been fabricated which comprise planar microfluidic channels incorporated into a microchip. However, the inefficiencies of multiple required passes of an analytical light beam through such microfluidic channels still remain.

SUMMARY OF THE INVENTION

There is a continuing need for microfluidic sensors that facilitate the efficient analysis of small volumes of fluids. Among the desired features in such sensors are elimination of the need for light beams to make multiple passes through an analyte fluid, integration of microfluidic channels and optical analysis into a single microchip, and robust, lightweight construction.

In one embodiment according to the present invention, a microfluidic optical sensor is provided, comprising: an optical waveguide extending between an optical input port and an optical output port, said optical waveguide being capable of propagating light from said optical input port to said optical output port, said optical waveguide comprising an optical waveguide interaction region; a fluidic channel extending between a fluid input port and a fluid output port, said fluidic channel being capable of conducting a fluid from said fluid input port to said fluid output port, said fluidic channel comprising a fluidic channel region; said fluidic channel region being separated from said optical waveguide interaction region by an interposed spacing material having a thickness; said thickness being configured to transmit an evanescent field of said light through said spacing material between said optical waveguide interaction region and said fluidic channel region.

In another embodiment according to the present invention, a microfluidic optical sensor is provided, comprising: an optical waveguide extending between an optical input port and an optical output port, said optical waveguide being capable of propagating light from said optical input port to said optical output port; a fluidic channel extending between a fluid input port and a fluid output port, said fluidic channel being capable of conducting a fluid from said fluid input port to said fluid output port; an optical resonator separated from said optical waveguide by a first spacing material having a first thickness between the optical resonator and the optical waveguide; said first thickness being configured to transmit an evanescent field of said light through the first spacing material between said optical waveguide and said optical resonator; said fluidic channel comprising a fluidic cavity region separated from said optical resonator by a second spacing material having a second thickness between the fluidic cavity region and the optical resonator; said second thickness being configured to transmit an evanescent field of light through the second spacing material between said optical resonator and said fluidic cavity region.

In a further embodiment according to the present invention, a method of making a microfluidic optical sensor is provided, comprising the steps of: providing an optical waveguide extending between an optical input port and an optical output port, said optical waveguide being capable of propagating light from said optical input port to said optical output port, said optical waveguide comprising an optical waveguide interaction region; providing a fluidic channel extending between a fluid input port and a fluid output port, said fluidic channel being capable of conducting a fluid from said fluid input port to said fluid output port, said fluidic channel comprising a fluidic channel region; providing a spacing material, having a thickness, interposed between said fluidic channel region and said optical waveguide interaction region; and configuring said thickness to transmit an evanescent field of said light through said spacing material between said optical waveguide interaction region and said fluidic channel region.

In an additional embodiment according to the present invention, a method of making a microfluidic optical sensor is provided, comprising the steps of: providing an optical waveguide extending between an optical input port and an optical output port, said optical waveguide being capable of propagating light from said optical input port to said optical output port; providing a fluidic channel extending between a fluid input port and a fluid output port, said fluidic channel being capable of conducting a fluid from said fluid input port to said fluid output port, said fluidic channel comprising a fluidic cavity region; providing an optical resonator separated from said optical waveguide by a first spacing material having a first thickness between the optical resonator and the optical waveguide; configuring said first thickness to transmit an evanescent field of said light through the first spacing material between said optical waveguide and said optical resonator; providing a second spacing material having a second thickness separating said fluidic cavity region and said optical resonator; and configuring said second thickness to transmit an evanescent field of light through the second spacing material between said optical resonator and said fluidic cavity region.

A more complete understanding of the present invention, as well as other features and advantages of the invention, will be apparent from the following detailed description and the accompanying drawings.

DETAILED DESCRIPTION

The present invention will now be described more fully with reference to the accompanying drawings, in which several presently preferred embodiments of the invention are shown. This invention may, however, be embodied in various forms and should not be construed as being limited to the embodiments set forth herein.

The present invention provides microfluidic optical sensors and methods for making and using the same. The microfluidic optical sensors facilitate interaction between a fluid to be subjected to optical detection, and light that is employed in the detection. The microfluidic optical sensors provide a high level of interaction between the evanescent field of detector light and a small amount of analyte fluid. Hence, the microfluidic optical sensors provide high detection sensitivity. Small volumes of analyte fluids, as well as analyte fluids comprising small concentrations of target analytes, can thus be effectively analyzed by the microfluidic optical detectors.

Figure 1:
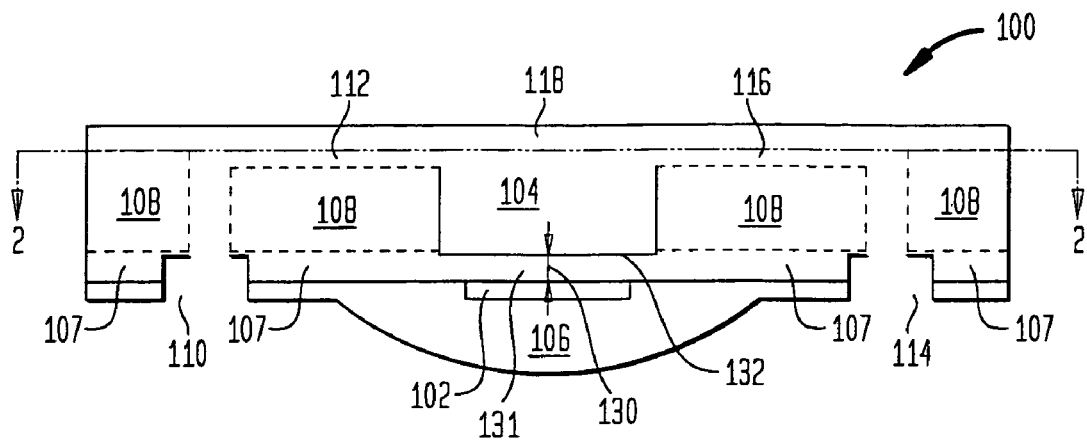
FIG. 1 shows a cross-sectional side view of an exemplary microfluidic optical sensor according to the present invention.

FIG. 1 shows a cross-sectional side view of an exemplary microfluidic optical sensor 100 according to the present invention. The sensor 100 comprises an optical waveguide 102 integrated with a fluidic channel 104. By "channel" is meant a cavity through which a fluid can pass. The cavity can be occupied, for example, by air, another gas, or a porous material. The optical waveguide 102 is bounded by a cladding layer 106 and a bottom cladding layer 107, the bottom cladding layer 107 having an overlaying substrate 108. A fluid input 110 communicates with fluidic channel 104 by a fluid conduit 112. A fluid output 114 communicates with fluidic channel 104 by a fluid conduit 116. A cover 118 is sealed to the substrate 108, and forms a flow directing path for a fluid together with the fluid conduits 112 and 116 and the fluidic channel 104.

Figure 2:
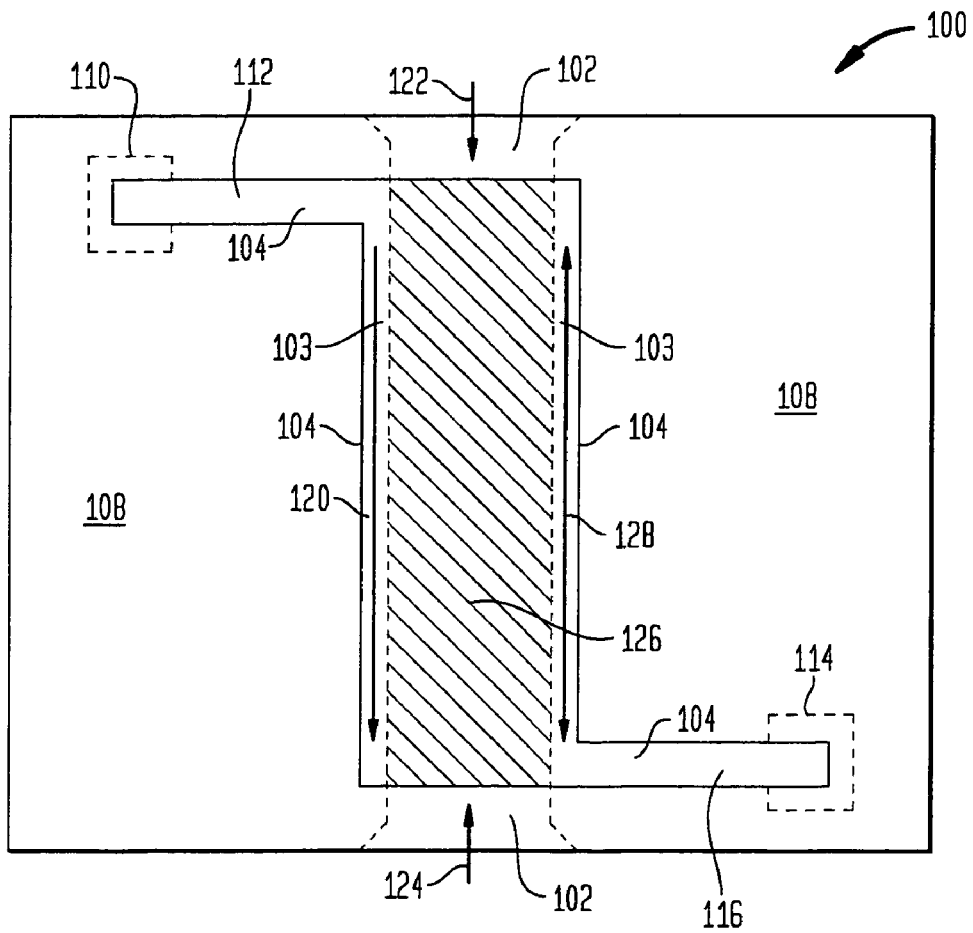
FIG. 2 shows a cross-sectional top view of the microfluidic optical sensor of FIG. 1.

FIG. 2 shows a cross-sectional top view of the microfluidic optical sensor 100 taken on line 2-2 shown in FIG. 1. The sensor 100 comprises a fluidic channel 104 communicating with a fluid input 110 and a fluid output 114 by fluid conduits 112 and 116, respectively. The fluidic channel 104 and the fluid conduits 112 and 116 are bounded by substrate 108. The fluidic channel 104 overlies the optical waveguide 102 within an optical waveguide interaction region 126.

The optical waveguide 102 is fabricated from a material having a relatively higher index of refraction that is suitable to serve as a waveguide core for the propagation of light. The term "light" means radiation having a wavelength or wavelengths in the infrared, visible, and/or ultraviolet spectra and suitable to propagate in the optical waveguide 102. The term "optical" means "of or relating to light". The cladding layer 106, the bottom cladding layer 107 and the substrate 108 are fabricated from a material or materials having a relatively lower index of refraction that is suitable to serve as a waveguide cladding to facilitate the propagation of the light in the optical waveguide 102. The cover 118 is fabricated from a material that is suitable to be bonded to the substrate 108 and that is suitable, together with the substrate 108 and the bottom cladding layer 107, for confining a fluid within the fluidic channel 104 and the fluid conduits 112 and 116. In one embodiment, the optical waveguide 102 employed in the microfluidic optical sensors herein comprises silicon. In another embodiment, the cladding 106, bottom cladding 107 and substrate 108 employed in the microfluidic optical sensors herein comprise silicon dioxide, silicon nitride, silicon oxynitride, ceramics, plastics, or quartz. Exemplary plastics include polydimethylsiloxane, polymethylmethacrylate, and poly(ethylene-terephthalate-glycol). The cover 118 and other layers herein to be bonded to substrates may, for example, comprise a borosilicate glass such as Pyrex 7740.

In operation, a fluid to be subjected to analysis is input into the microfluidic optical sensor 100 through the fluid input 110. The fluid conduit 112 then carries the fluid into the fluidic channel 104, where the fluid then generally proceeds in the direction of the arrow 120. The fluid conduit 116 then carries the fluid to the fluid output 114. The fluid is then collected for any desired post-analysis treatment or use. Light is propagated through the optical waveguide 102 in the general direction of arrow 122 or arrow 124. In one embodiment, light is propagated in the general directions of both arrow 122 and arrow 124. In any of these exemplary embodiments and in other exemplary embodiments discussed elsewhere in this specification, light that is propagated through the optical waveguide 102 makes only a single pass through the waveguide. In alternative embodiments, such light may make multiple passes through the optical waveguide 102, but this practice generally is not required for effective, high sensitivity operation of the microfluidic optical sensor 100.

As shown in FIG. 2, a fluidic channel region 103 of the fluidic channel 104 overlies the optical waveguide 102 in the optical waveguide interaction region 126. Light propagates in the optical waveguide 102 in the general direction of arrow 122 or arrow 124. Both of arrows 122 and 124 are parallel with the general direction of arrow 120 indicating the general direction of flow of the fluid in the fluidic channel 104. The light and fluid generally propagate, in the optical waveguide 102 and the fluidic channel 104 respectively, in either the same direction or a countercurrent direction over the distance indicated by the double-ended arrow 128 longitudinally traversing the optical waveguide interaction region 126. In one embodiment, the linear distance 128 is up to about 10 centimeters (cm).

As shown in FIG. 1, the optical waveguide 102 and the fluidic channel 104 are separated by a spacing layer 131 having a thickness 130 constituting a region of the cladding layer 107 in the optical waveguide interaction region 126. The cladding layer 107 permits the evanescent field of light propagating in the optical waveguide 102 to penetrate to the substrate 108 and the fluidic channel 104 in the optical waveguide interaction region 126. The thickness 130 is designed so that some of the evanescent field penetrates into the fluidic channel 104 within the optical waveguide interaction region 126, where the light can interact with the surface 132 of the fluidic channel 104. Light also interacts with fluid flowing in the fluidic channel 104. The thickness 130 affects the extent to which the evanescent field interacts with the surface 132 and with the fluid in the fluidic channel 104. If the thickness 130 is too great, the evanescent field will not reach the surface 132 nor interact with the fluid in the fluidic channel 104. If the thickness 130 is too small, the propagation of the light in the optical waveguide 102 may be disturbed. In one embodiment, the thickness 130 is roughly equivalent to the wavelength of the light propagated in the optical waveguide 102. The cross-sectional shape of the fluidic channel 104 desirably is compatible with the optical mode within the optical waveguide 102. In an alternative embodiment, the bottom cladding layer 107 constitutes a region of the substrate 108.

The refractive indices near the surface 132 are influenced by the nature of a fluid that is input through fluid input 110, carried by the fluid conduit 112 into the fluidic channel 104, withdrawn by fluid conduit 116 and then output through fluid output 114. Hence, changes in such refractive indices cause changes in the light from the evanescent field that interacts with the surface 132 and with the fluid. These changes alter the optical path length and accordingly the phase of the light in the waveguide 102.

Further, the optical absorption and transmission characteristics of the surface 132 and of fluid within the fluidic channel 104 are influenced by the nature of a fluid that is input through fluid input 110, carried by the fluid conduit 112 into the fluidic channel 104, withdrawn by fluid conduit 116 and output through fluid output 114. Changes in such absorption and transmission accordingly change the wavelength spectrum of the light originating from the evanescent field that interacts with the surface 132 and with the fluid.

Light that is output from the microfluidic optical sensor in the direction 122 or 124, including light that has interacted with the surface 132 and with fluid flowing in the fluidic channel 104, can then be subjected to analysis for detection of phase changes, detection of polarization changes, detection of polarization mode dispersion changes, and detection of changes in the wavelength spectrum. In one embodiment, such light is input into a Mach-Zehnder interferometer for detection of phase changes induced by interaction of the evanescent field with the surface 132 and with fluid within the fluidic channel 104. For example, a Mach-Zehnder interferometer can be integrated together with the microfluidic optical sensor 100 into a monolithic planar array comprising optical waveguide 102 bounded by cladding layer 106, bottom cladding layer 107, and substrate 108. In a further embodiment, the microfluidic optical sensor 100 can itself be configured as a Mach-Zehnder interferometer. These integrated embodiments may provide for increased sensor accuracy, as all of the sensor components so integrated are subjected in a uniform manner to external stress such as temperature fluctuations. In another embodiment, light that is output from the microfluidic optical sensor 100 in the direction 122 or 124 can then be input into a spectrophotometer for detection of changes in the wavelength spectrum.

The nature of the fluid to be carried through the fluidic channel 104 for analysis by the microfluidic optical sensor 100 is a matter of the sensor operator's choice. For example, the fluid may be a liquid, a gas, a suspension of particles in a fluid, an emulsion, a solution, or a dispersion. The viscosity of the fluid desirably is suitable to facilitate flow of the fluid through the fluidic channel 104. For example, if the fluid viscosity is too high, or if the size or concentration of particles or other solids in the fluid is too great, clogging may result or residue may be retained in the microfluidic optical sensor 100. The fluid may be aqueous or nonaqueous, and organic or inorganic. The fluid may contain oligomers, polymers, or macromolecules. The fluid may contain biological analytes such as proteins, carbohydrates, fats, ribonucleic acids, bacteria, cells or viruses. The surface 132 can, if desired, be provided with a bound or otherwise fixed agent that will also selectively bind with components of or otherwise interact with the fluid carried in the fluidic channel 104. For example, the surface 132 can be provided with bound antibodies adapted to selectively bind with and therefore enable detection of target antigens in the fluid. The target antigens can, for example, be tagged with a fluorescent, radioactive or chromophoric agent, so that the fluorescence, radioactivity or color change of antigens bound to the antibodies can be detected. Other biological and chemical binding regimes, such as proteins and protein receptors, or mutually-reactive chemical moieties, can also be used. Further, chemical and biological markers can be allowed to selectively bind or otherwise interact or react with components of a fluid to be analyzed, thus selectively changing the refractive index and light absorption profiles of the fluid itself.

Figure 3:
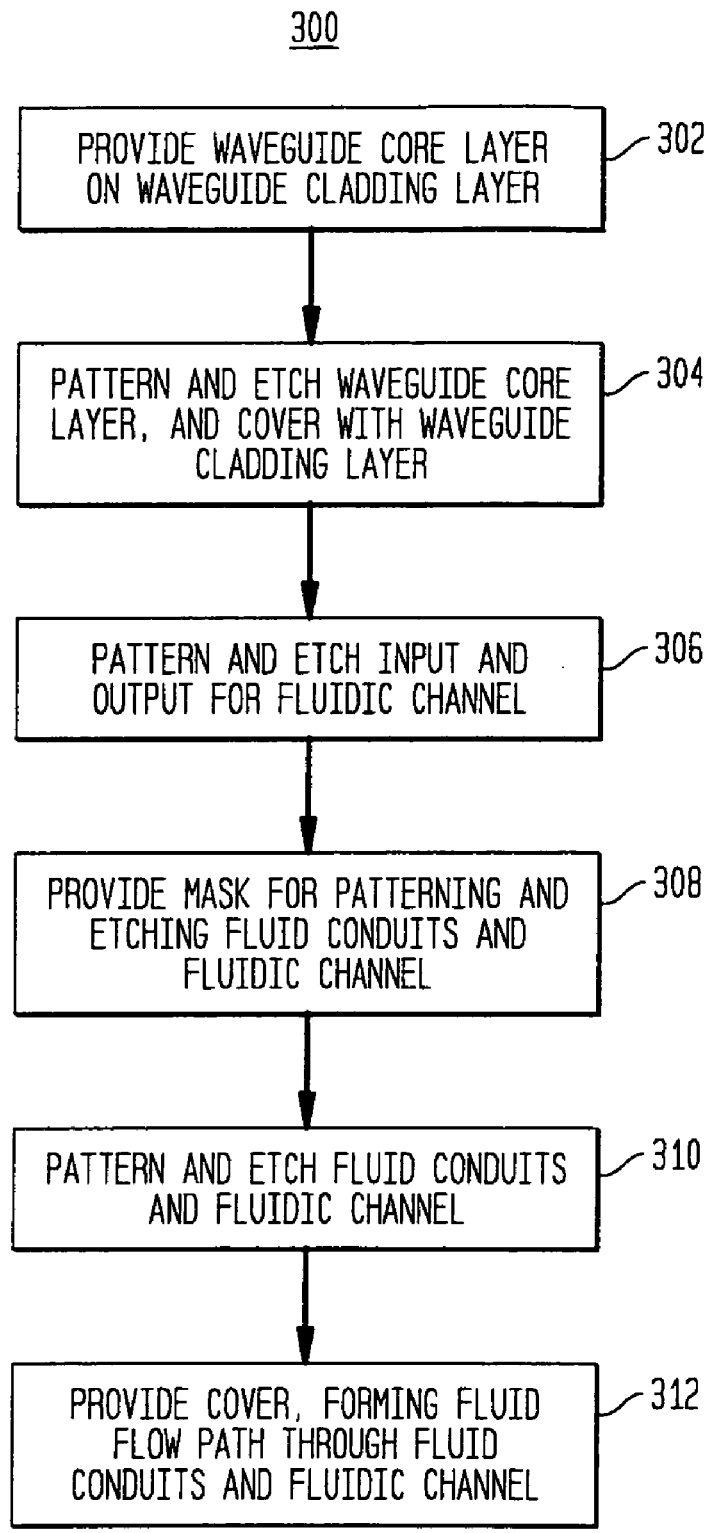
FIG. 3 shows the steps of an exemplary process for fabrication of the microfluidic optical sensor shown in FIGS. 1 and 2.
Figure 4:
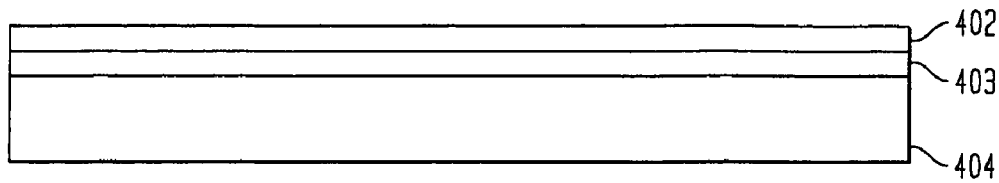
FIGS. 4-8 show cross-sectional side views of a microfluidic optical sensor according to the present invention during various steps of its fabrication according to the process shown in FIG. 3.
Figure 5:
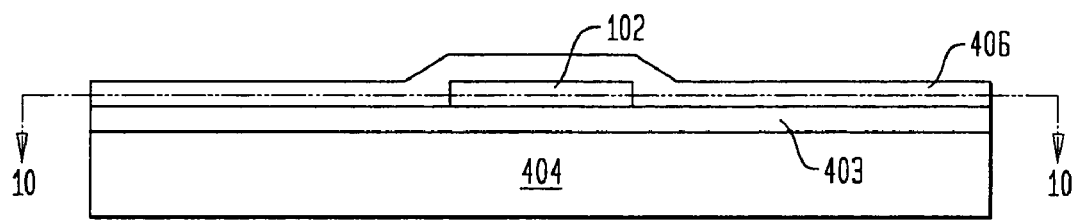
Figure 6:
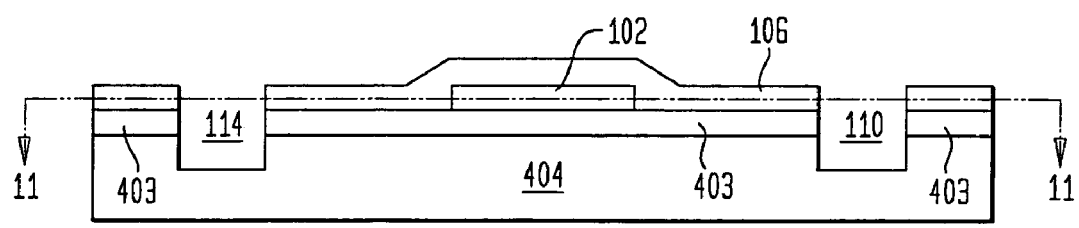
Figure 7:
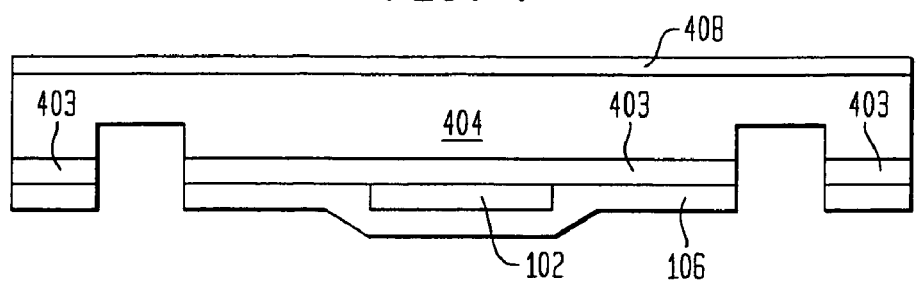
Figure 8:
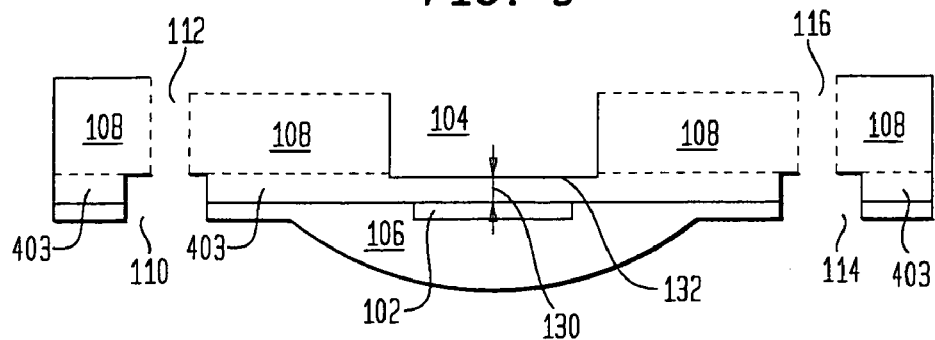
Figure 9:
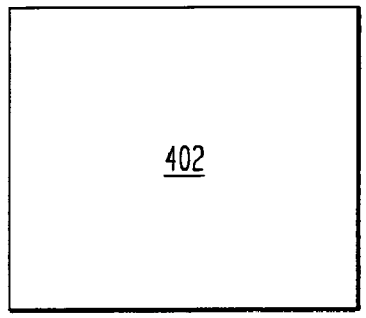
FIGS. 9-13 show top views of a microfluidic optical sensor according to the present invention during various steps of its fabrication according to the process shown in FIG. 3.
Figure 10:
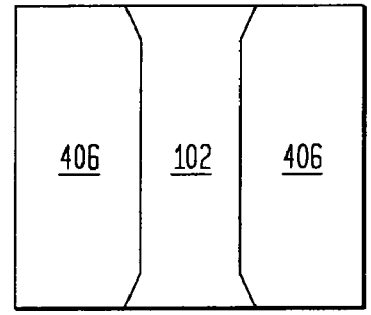
Figure 11:
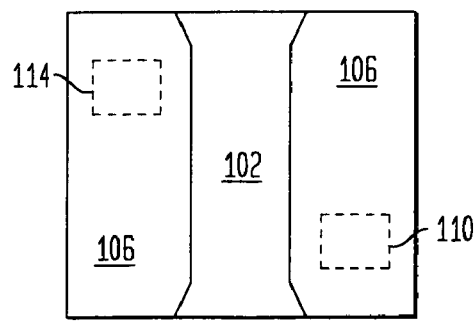
Figure 12:
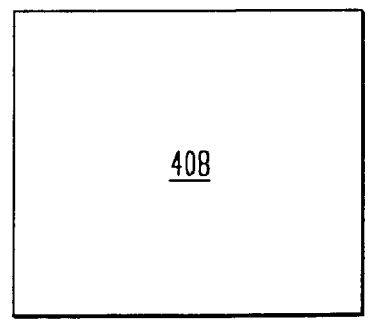
Figure 13:
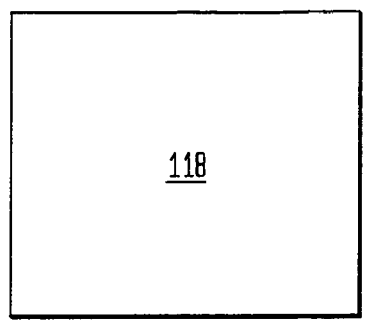

FIG. 3 shows the steps of an exemplary process 300 that is suitable for fabrication of the microfluidic optical sensor 100. FIGS. 4-8 together with FIG. 1 show cross-sectional side views and FIGS. 9-13 together with FIG. 2 show top views of the microfluidic optical sensor 100 during various steps of its fabrication according to the exemplary process 300 shown in FIG. 3. Referring to FIG. 3, in step 302 a waveguide core layer 402 having a relatively higher refractive index is provided on a waveguide cladding layer 404 having a relatively lower refractive index as shown in cross-sectional side view in FIG. 4 and top view in FIG. 9. In one embodiment, step 302 comprises the provision of a bottom cladding layer 403 interposed between the layers 402 and 404. The bottom cladding layer serves to define and permit precise control over the thickness 130 discussed earlier, and also serves as an etch stop for the preparation of the fluidic channel as also discussed below. In step 304 the waveguide core layer 402 is patterned and etched to form the optical waveguide 102 and is covered with a waveguide cladding layer 406 having a relatively lower refractive index as shown in cross-sectional side and top views in FIGS. 5 and 10 respectively, the latter figure being taken on line 10-10 shown in FIG. 5. In step 306, fluid input 110 and fluid output 114 are patterned and etched as shown in cross-sectional side view in FIG. 6 and top view in FIG. 11, the latter figure being taken on line 11-11 shown in FIG. 6. Formation of cladding layer 106 is also thus completed. In step 308, the backside of the cladding layer 404 opposite to that on which the optical waveguide 102 is formed, is then provided with a masking layer 408 suitable for subsequent patterning and etching of such surface to form the fluid conduits 112 and 116 and the fluidic channel 104, as shown in cross-sectional side view in FIG. 7 and in top view in FIG. 12. In step 310, the masking layer 408 is patterned, etched and then removed, to form the fluid conduit 112, fluidic channel 104, and fluid conduit 116, as shown in cross-sectional FIGS. 8 and 2, and fabrication of the substrate 108 is completed. The bottom cladding layer 403 serves as an etch stop in formation of the fluidic channel 104, terminating the etching at the surface 132. Hence, the bottom cladding layer 403 also effectively defines and controls the distance 130. In step 312, as shown in cross-sectional side view in FIG. 1 and top view in FIG. 13, a cover 118 is sealed to the substrate 108, forming a flow directing path for a fluid together with the fluid conduits 112 and 116 and the fluidic channel 104.

The exemplary steps of FIG. 3 can be carried out, for example, using semiconductor chip fabrication processes adapted to the materials selected for making the microfluidic optical sensor 100 as earlier discussed. The steps of FIG. 3 are merely exemplary, and it is to be understood that such steps can readily be carried out in different manners or orders. It is further understood that the various elements of the microfluidic optical sensor 100 can be built up, patterned and etched by using analogous steps carried out in analogous process routines, or otherwise fabricated, in order to produce the same or a similar device structure. Background information is provided in Verpoorte, Elizabeth, et al., "Microfluidics Meets MEMS," *Proceedings of the IEEE*, Vol. 91, No. 6, June 2003, pp. 930-948, the entirety of which is hereby incorporated herein by reference.

Figure 14:
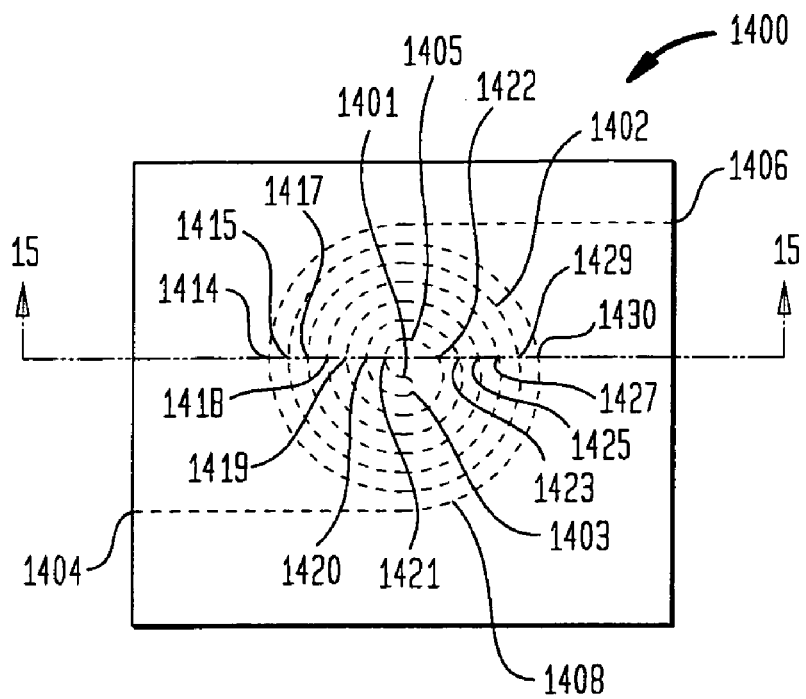
FIG. 14 shows a cross-sectional top view of a microfluidic optical sensor according to the present invention.

FIG. 14 shows a cross-sectional top view of an exemplary microfluidic optical sensor 1400 according to the present invention. The sensor 1400 comprises an optical waveguide 1402 in the form of a spiral doubled over upon itself. The optical waveguide 1402 comprises a first end 1404 and a second end 1406. In this exemplary embodiment, the first end 1404 serves as an optical input and the second end 1406 serves as an optical output. The first end 1404 and the second end 1406 together form an outermost double loop 1408 of the optical waveguide 1402, and take the form of smooth curves without any sharp directional changes in order to avoid undue attenuation of light propagating in the optical waveguide 1402. The outermost double loop 1408 leads continuously inward toward the center 1401 of the spiral of the optical waveguide 1402, through a plurality of inner loops having successively smaller diameters, terminating in an S-shaped link 1403 between the portions of an innermost double loop respectively connected to the first end 1404 and the second end 1406. In one embodiment, the length of the path along the optical waveguide 1402 between the first end 1404 and the second end 1406 is up to about 0.2 meter. In another embodiment, the length of the path along the optical waveguide 1402 between the first end 1404 and the second end 1406 is up to about two (2) meters. As the path length increases, so does the sensitivity of the microfluidic optical detector 100. In one embodiment, the diameter of the outermost double loop 1408 is within a range of between about one and about five cm, and the diameter of the innermost double loop 1405 is within a range of between about one and about ten millimeters (mm).

Figure 16:
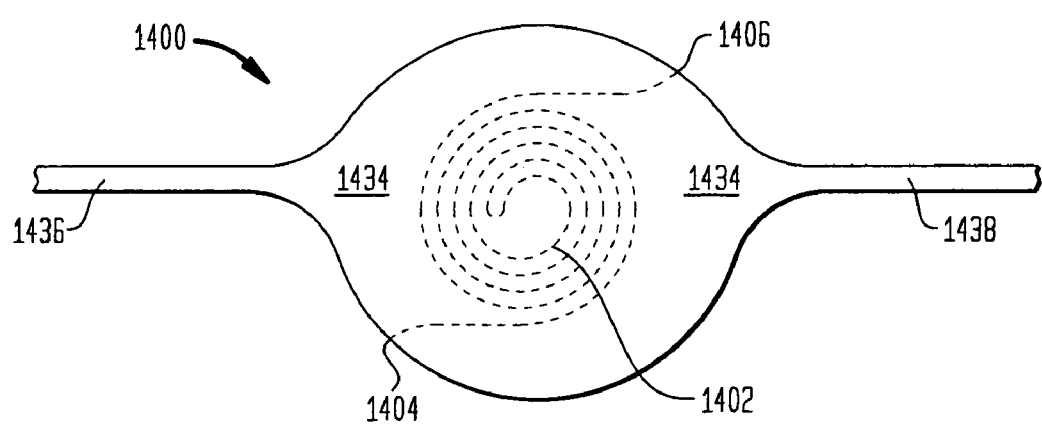
FIG. 16 shows a further cross-sectional top view of the microfluidic optical sensor of FIG. 14.
Figure 15:
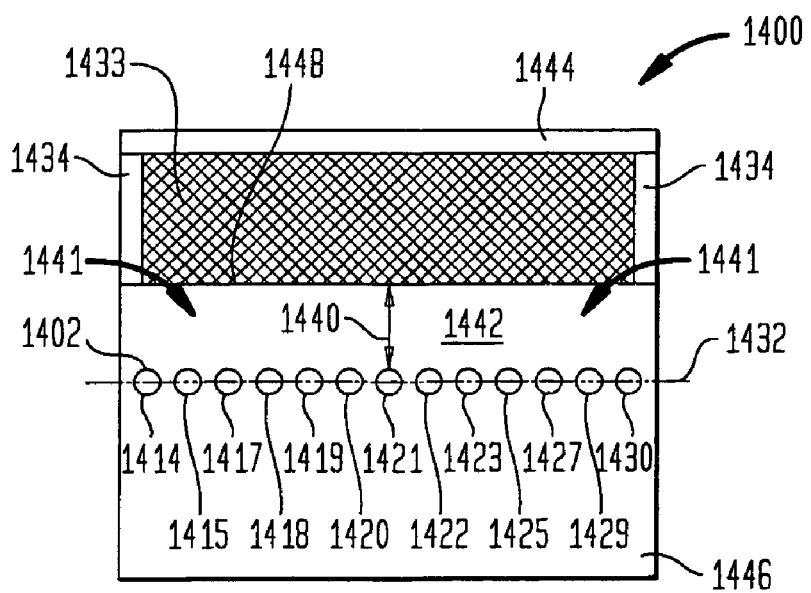
FIG. 15 shows a cross-sectional side view of the microfluidic optical sensor of FIG. 14.

FIG. 15 shows a cross-sectional side view of the microfluidic optical sensor 1400 taken on line 15-15 shown in FIG. 14. Portions 1414, 1415, 1417, 1418, 1419, 1420, 1421, 1422, 1423, 1425, 1427, 1429, and 1430 of the optical waveguide 1402, visible in both FIGS. 14 and 15, are in a spaced apart arrangement in a plane indicated by line 1432, collectively forming an optical waveguide interaction region 1441. FIG. 16 shows a further top cross-sectional view of the microfluidic optical sensor 1400. The spiral of the optical waveguide 1402 is integrated with and overlaid by a fluidic channel region 1433 constituting a portion of a fluidic channel 1434 having an input 1436 and an output 1438. The fluidic channel 1434 is overlaid by a cover 1444. Referring to FIG. 15, the fluidic channel 1434 is spaced apart from the plane 1432 of the optical waveguide 1402 by a cladding layer 1442 at a distance 1440. The spiral of the optical waveguide 1402 is underlaid by a substrate 1446.

The optical waveguide 1402 is fabricated from a material having a relatively higher index of refraction that is suitable to serve as a waveguide core for the propagation of light. The cladding layer 1442 and the substrate 1446 are fabricated from materials having relatively lower indices of refraction that are suitable to serve as waveguide claddings to facilitate the propagation of light in the optical waveguide 1402. The cover 1444 is fabricated from a material that is suitable to be bonded to the cladding layer 1442 and that is suitable, together with the cladding layer 1442, for confining a fluid within the fluidic channel 1434.

In operation, a fluid to be subjected to analysis is input into the microfluidic optical sensor 1400 through the fluid input 1436. The fluid fills the fluidic channel 1434 and is then carried to the fluid output 1438. The fluid is then collected for any desired post-analysis treatment or use. Light is propagated through the optical waveguide 1402 from the first end 1404 to the second end 1406. In one alternative embodiment, light is propagated through the optical waveguide 1402 from the second end 1406 to the first end 1404. In another alternative embodiment, light is propagated both from the first end 1404 to the second end 1406, and from the second end 1406 to the first end 1404. In a further alternative embodiment, 1436 serves as the fluid output, and 1438 serves as the fluid input.

As shown in FIG. 16, the fluidic channel 1434 overlies the optical waveguide 1402. Light propagates in the optical waveguide 1402 in the general direction from the first end 1404 to the second end 1406. As shown in FIG. 15, the optical waveguide 1402 and the fluidic channel 1434 are separated at a distance 1440 by a spacing layer constituted by the cladding layer 1442. The cladding layer 1442 is thin enough across the distance 1440 to permit the evanescent field of light in the optical waveguide interaction region 1441 of the optical waveguide 1402 to penetrate into the fluidic channel region 1443 of the fluidic channel 1434. There, the light can interact with the surface 1448 of the fluidic channel 1434 and the fluid flowing in the fluidic channel 1434. This light can be analyzed in a manner analogous to that discussed above in connection with the microfluidic optical sensor 100. The interaction path length through the optical waveguide 1402 is approximately given by the formula $L_i = 2\pi N r$, where N is the number of single loops (each double loop constituting two single loops) and r is the mean radius of the outermost loop 1408.

Figure 17:
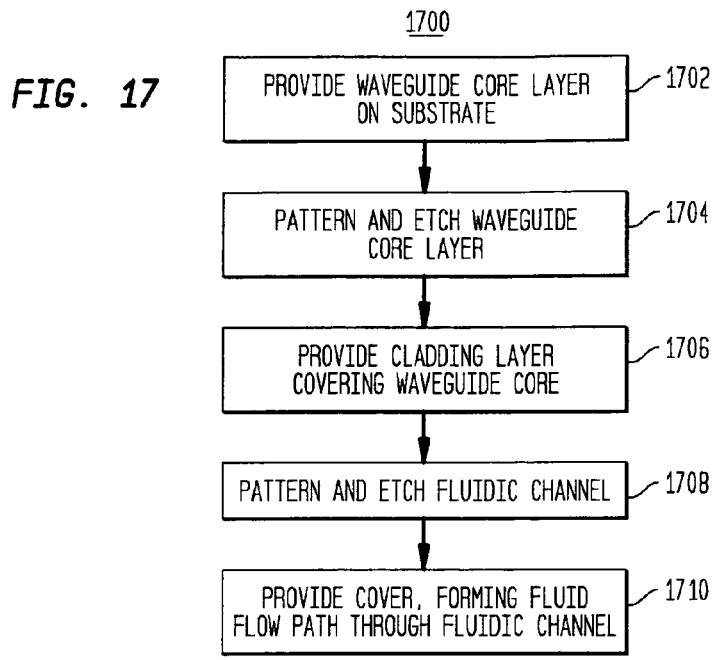
FIG. 17 shows the steps of a process for fabrication of the microfluidic optical sensor shown in FIG. 14.

FIG. 17 shows the steps of an exemplary process 1700 that is suitable for fabrication of the microfluidic optical sensor 1400. In step 1702 a waveguide core layer having a relatively higher refractive index is provided on a substrate 1446 having a relatively lower refractive index as shown in FIG. 15. In step 1704 the waveguide core layer is patterned and etched to form the optical waveguide 1402 as shown in FIGS. 14 and 15. In step 1706 the optical waveguide 1402 is covered with a waveguide cladding layer 1442 having a relatively lower refractive index as shown in FIG. 15. In step 1708, the fluidic channel 1434 is patterned and etched into the waveguide cladding layer 1442 as shown in FIGS. 15 and 16. In step 1710, as shown in FIG. 15, a cover 1444 is sealed to the cladding layer 1442, forming a flow directing path for a fluid together with the fluidic channel 1434. The exemplary steps of FIG. 17 can be carried out, for example, using semiconductor chip fabrication processes adapted to the materials selected for making the microfluidic optical sensors as earlier discussed. The steps of FIG. 17 are merely exemplary, and it is to be understood that such steps can readily be carried out in different manners and orders, and that the various elements of the microfluidic optical sensor 1400 can be built up, patterned and etched, or otherwise fabricated, by using analogous steps carried out in analogous process routines in order to produce the same or a similar device structure.

Figure 18:
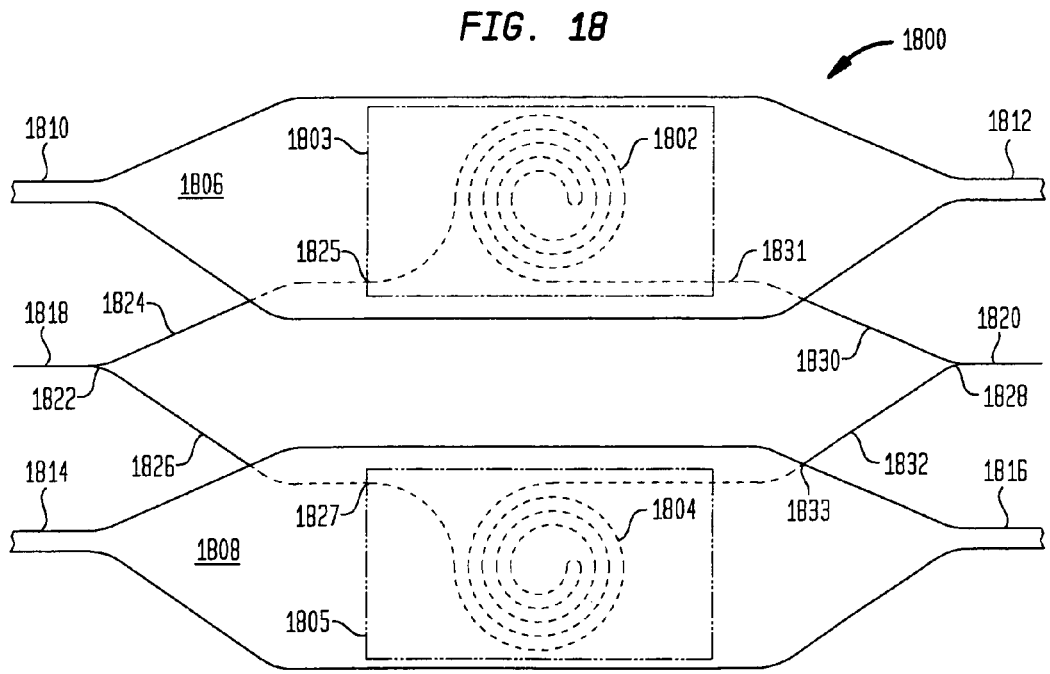
FIG. 18 shows a cross-sectional top view of a microfluidic optical sensor according to the present invention.

FIG. 18 shows a cross-sectional top view of an exemplary microfluidic optical sensor 1800 according to the present invention. The sensor 1800 comprises two spiral optical waveguides 1802 and 1804, each doubled over onto itself in the same manner as discussed above in connection with the optical waveguide 1402 shown in FIG. 14. As shown in FIG. 18, the fluidic channel 1806 overlies the optical waveguide 1802, and the fluidic channel 1808 overlies the optical waveguide 1804. Each of the spiral optical waveguides 1802 and 1804 is incorporated into a structure analogous to that discussed above in connection with FIGS. 14 and 15, facilitating analogous interaction of evanescent field light with the respective fluidic channels 1806 and 1808. Fluidic channel 1806 comprises input port 1810, and output port 1812. Fluidic channel 1808 comprises input port 1814, and output port 1816. Desirably, fluidic channel 1806 has a flow channel slightly larger than and approximating the perimeter of spiral optical waveguide 1802 as shown within the region 1803. Desirably, fluidic channel 1808 has a flow channel slightly larger than and approximating the perimeter of spiral optical waveguide 1804 as shown within the region 1805. The sensor 1800 further comprises an optical waveguide input 1818, and an optical waveguide output 1820. An optical splitter 1822 provides two waveguide outputs from the optical waveguide input 1818. Waveguide 1824 connects one of such waveguide outputs to an input 1825 to spiral optical waveguide 1802, and waveguide 1826 connects the other of such waveguide outputs to an input 1827 to spiral optical waveguide 1804. An optical coupler 1828 combines two optical inputs into optical waveguide output 1820. Optical waveguide 1830 connects an output 1831 from spiral waveguide 1802 to one of such optical inputs. Optical waveguide 1832 connects an output 1833 from spiral waveguide 1804 to the other of such optical inputs.

In operation of the sensor 1800, a fluid containing components to be analyzed is carried through fluidic channel 1806, from input port 1810 to output port 1812. A reference fluid is carried through fluidic channel 1808, from input port 1814 to output port 1816. Light is input at port 1818 and split into two portions by optical splitter 1822. Optical waveguide 1824 carries one of such portions to the input 1825 to spiral 1802. Optical waveguide 1826 carries the other of such portions to the input 1827 to spiral 1804. Optical waveguide 1830 carries light from the output 1834 from spiral 1802 to an input to coupler 1828. Optical waveguide 1832 carries light from the output 1833 from spiral 1804 to the other input to coupler 1828. Thus, the microfluidic optical sensor 1800 can be operated as a Mach-Zehnder interferometer in order to detect a relative phase shift between the two optical arms of the interferometer generated at optical waveguides 1824 and 1826, as induced by the nature of a fluid being analyzed by the sensor 1800. A phase change in the light output on optical waveguide 1820 is indicative of the refractive index of the analyte fluid passed through fluidic channel 1806.

In an alternative embodiment, the spiral 1804 and the fluidic channel 1808 are omitted. In this embodiment, waveguides 1826 and 1832 are directly connected together to create a waveguide path having a defined length between the optical splitter 1822 and optical coupler 1828. The length of such waveguide path can be selected to generate, for example, a fixed phase shift. In a further embodiment, the spiral 1804 is included, and the fluidic channel 1808 is omitted. In this latter embodiment, a long optical path through the spiral 1804 between waveguides 1826 and 1832 is created. The length of such waveguide path can be selected to serve, for example, as a fixed control or otherwise result in desired interferometer performance.

Figure 19:
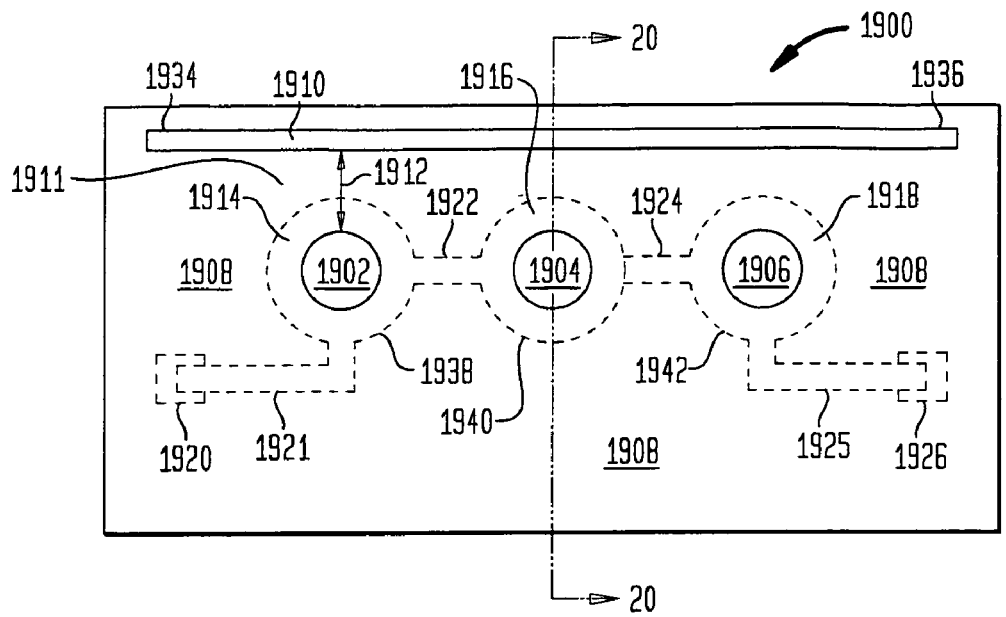
FIG. 19 shows a cross-sectional top view of a microfluidic optical sensor according to the present invention.
Figure 20:
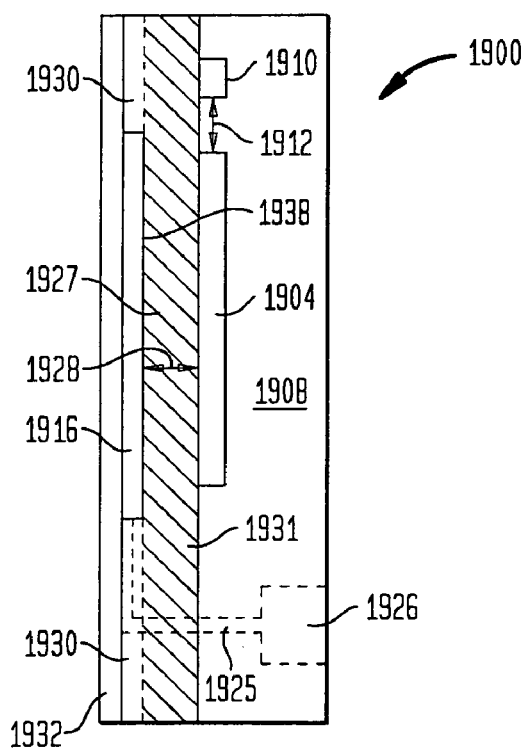
FIG. 20 shows a cross sectional side view of the microfluidic optical sensor shown in FIG. 19.

FIG. 19 shows a cross-sectional top view of an exemplary microfluidic optical sensor 1900 according to the present invention. The microfluidic optical sensor 1900 comprises a plurality of optical resonators 1902, 1904, and 1906 having a disc shape or other desired shape, fabricated from a material suitable for forming an optical waveguide core and having a relatively higher refractive index than the surrounding matrix. In particular, the optical resonators 1902-1906 are bounded by a cladding layer 1908 having a relatively lower refractive index. An optical waveguide 1910 is integrated with and spaced apart from the optical resonators by a spacing layer 1911 constituting a region of the cladding layer 1908, at a minimum distance 1912. A fluidic channel comprising a plurality of fluidic channel regions 1914, 1916 and 1918 having perimeters generally corresponding to but slightly larger than those of the optical resonators 1902, 1904 and 1906, respectively, is integrated with and underlies such optical resonators. In one embodiment, the perimeters of the fluidic channel regions 1914, 1916 and 1918 are defined by average diameters within a range of between about 0.1 mm and about 1 mm. In another embodiment, the diameters of the fluidic channel regions 1914, 1916 and 1918 are up to about ten microns. Further embodiments have other diameters within a range between about ten microns and about 0.1 mm. A fluid input 1920 enables injection of a fluid into the fluidic channel region 1914 through a fluid conduit 1921. A fluid conduit 1922 enables fluid to be conveyed from the fluidic channel region 1914 into the fluidic channel region 1916. A fluid conduit 1924 enables fluid to be conveyed from the fluidic channel region 1916 into the fluidic channel region 1918. A fluid output 1926 enables ejection of a fluid through a fluid conduit 1925 from the fluidic channel region 1918. FIG. 20 shows a cross sectional side view of the microfluidic optical sensor 1900 taken on line 20-20 shown in FIG. 19. The fluidic channel region 1916 is shown adjacent to the optical resonator 1904, spaced apart by a distance 1928. The fluidic channel regions 1914, 1916 and 1918 are bounded by the substrate 1930 also underlying the optical waveguide 1910 and the optical resonator 1904. FIG. 20 shows the optical waveguide 1910 and the optical resonator 1904 spaced apart from the fluidic channel region 1916 by a spacing layer 1927 constituting a region of the substrate 1930 by the distance 1912. The spacing layer 1927 can alternatively be constituted by a bottom cladding layer 1931 interposed between the cladding layer 1908 and the substrate 1930. A cover layer 1932 is positioned adjacent to the substrate 1930, and also forms a flow-directing path for a fluid together with the fluid conduits 1921, 1922, 1924 and 1925, and the fluidic channel regions 1914, 1916 and 1918.

In operation, fluid is input by the fluid input 1920 through fluid conduit 1921 into fluidic channel region 1914. The fluid then successively flows by fluid conduit 1922 into fluidic channel region 1916, and by fluid conduit 1924 into fluidic channel region 1918. The fluid is then output through fluid conduit 1925 to the fluid output 1926 and collected for any desired post-analysis treatment or use. Light is input into the optical waveguide 1910 from the optical input point 1934. As the light propagates in the optical waveguide 1910 toward the optical output point 1936, the cladding layer 1908 permits the evanescent field of light in the optical waveguide 1910 to couple across the distance 1912 into the optical resonators 1902, 1904, and 1906, each of which constitutes an optical waveguide interaction region. As the light resonates in the optical resonators 1902, 1904 and 1906, the substrate 1930 permits a portion of an evanescent field of the light in the optical resonators 1902, 1904 and 1906 to penetrate across the distance 1928 to the surfaces 1938, 1940 and 1942 of the fluidic channel regions 1914, 1916 and 1918, respectively. The evanescent field of such light can interact with the surfaces 1938, 1940 and 1942 as well as with fluid flowing within the fluidic channel regions 1914, 1916 and 1918. The interaction path within each of the fluidic channel regions 1914, 1916 and 1918 can be approximately expressed by the formula, $L_i = c\tau_c = \lambda Q/2\pi$, where $\tau_c$ is the channel region lifetime, c is the speed of light, and Q is a unitless quality factor indicative of the light reflective capability of the perimeters of the optical resonators 1902, 1904 and 1906. A high Q corresponds to a highly confining optical cavity where light bounces inside the cavity many times before exiting. Typical values of high Q are within a range of between about $10^4$ and about $10^6$. Light from the waveguide 1910 as output at point 1936 including light that has interacted with the surfaces 1938, 1940 and 1942 and with fluid flowing in the fluidic channel regions 1914, 1916 and 1918 can then be subjected to analysis for detection of phase changes, and changes in the wavelength spectrum, in the same manner as earlier discussed.

In one embodiment comprising optical resonators 1902, 1904 and 1906, the microfluidic optical sensor 1900 has a relatively small bandwidth, for example within a range of between about 1.0 nanometer (nm) and 0.1 nm, and is accordingly equipped with a narrow linewidth stabilized laser light source. In general, microfluidic optical sensors that do not incorporate resonators may have a relatively large bandwidth, on the order of about 100 nm, and therefore may be more practical to implement because they may not need a narrow linewidth stabilized laser source.

The optical waveguide 1910 and the optical resonators 1902, 1904 and 1906 are fabricated from materials having relatively higher indices of refraction that are suitable to serve as waveguide cores for the propagation of light. The cladding layer 1908, the cladding layer 1931 and the substrate 1930 are fabricated from materials having relatively lower indices of refraction that are suitable to serve as waveguide claddings to facilitate the propagation of light at wavelengths that propagate in optical waveguide 1910. The cover 1932 is fabricated from a material that is suitable to be bonded to the substrate 1930 and that is suitable, together with the substrate 1930 and the cladding layer 1931, for confining a fluid within the fluidic channel regions 1914, 1916 and 1918, and the fluid conduits 1921, 1922, 1924 and 1925.

Figure 21:
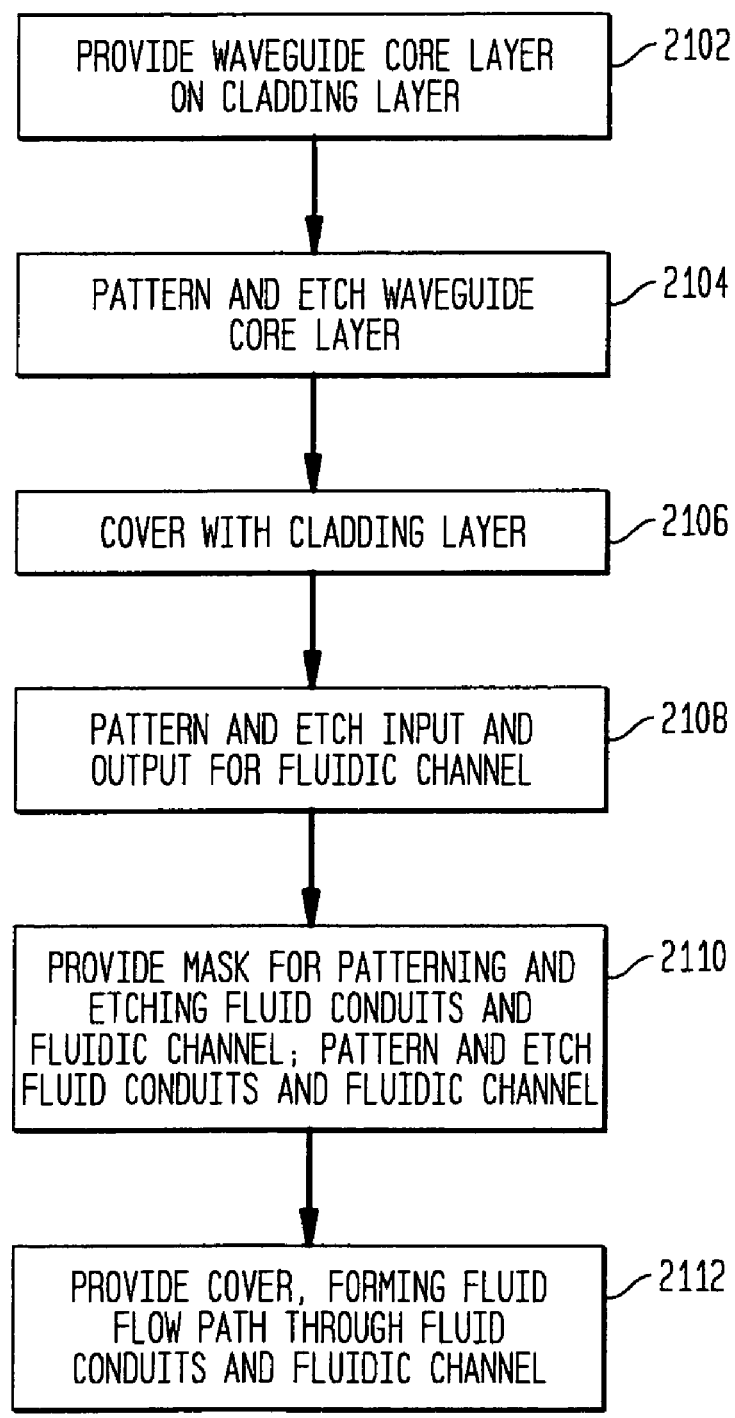
FIG. 21 shows the steps of an exemplary process for fabrication of the microfluidic optical sensor shown in FIG. 19.

FIG. 21 shows the steps of an exemplary process 2100 that is suitable for fabrication of the microfluidic optical sensor 1900. In step 2102 a waveguide core layer having a relatively higher refractive index is provided on a waveguide cladding layer having a relatively lower refractive index, which may include an interposed bottom cladding layer as earlier discussed. In step 2104 the waveguide core layer is patterned and etched to form the optical waveguide 1910 and the optical resonators 1902, 1904 and 1906. In step 2106 the optical waveguide 1910 and the optical resonators 1902, 1904 and 1906 are covered with a waveguide cladding layer 1908 having a relatively lower refractive index as shown in FIG. 20. In step 2108, the liquid input 1920 and the liquid output 1926 are patterned and etched into the waveguide cladding layer 1908 as shown in FIGS. 19 and 20. In step 2110, the substrate 1930 is patterned and etched to form the fluidic channel regions 1914, 1916 and 1918, and the fluid conduits 1921, 1922, 1924 and 1925 as shown in FIGS. 19 and 20. In step 2112 as shown in FIG. 20, a cover 1932 is sealed to the substrate 1930, forming a flow directing path for a fluid together with the fluidic channel regions 1914, 1916 and 1918, and the fluid conduits 1921, 1922, 1924 and 1925. The exemplary steps of FIG. 21 can be carried out, for example, using semiconductor chip fabrication processes adapted to the materials selected for making the microfluidic optical sensor as earlier discussed. The steps of FIG. 21 are merely exemplary, and it is to be understood that such steps can readily be carried out in different manners and orders, and that the various elements of the microfluidic optical sensor 1900 can be built up, patterned and etched, or otherwise fabricated, by using analogous steps carried out in analogous process routines in order to produce the same or a similar device structure.

The microfluidic optical sensors can, for example, be incorporated into systems comprising further elements. For example, such sensors can be incorporated into monolithic planar systems formed on microchips in order to facilitate further processing of the light and of the fluid as discussed herein.

While the present invention has been disclosed in a presently preferred context, it will be recognized that the present teachings may be adapted to a variety of contexts consistent with this disclosure and the claims that follow. For example, the optical and fluid paths shown in FIG. 2 can have the same or different lengths, such lengths being chosen in the fabricator's discretion, and do not have to be mutually parallel or coextensive. Input and output conduits can be located in positions other than as shown in FIGS. 1 and 2. Microfluidic optical sensors similar to that shown in FIGS. 1 and 2 but comprising multiple waveguides and/or fluidic channels, which may or may not be mutually coextensive and aligned together in a sandwich, can be constructed. For example, the optical waveguide 102 can be sandwiched between two fluidic channels 104. For example, the spiral waveguide 1402 shown in FIG. 14 can be of any desired circumference and length, and can be arranged in a format other than the spiral doubled upon itself as shown in the figure, so long as the waveguide 1402 does not have sharp turns causing excessive optical attenuation and so long as it can be practically fabricated. The fluidic channel 1434 desirably overlays or underlays the entire footprint of the spiral as shown in FIGS. 14-16, but this is not essential. In an alternative embodiment, the spiral waveguide 1402 is sandwiched between two fluidic channels 1434. A further embodiment may comprise multiple spiral waveguides 1402 and/or multiple fluidic channels, which may or may not be mutually coextensive and aligned together in a sandwich. For example, the spiral waveguides 1802 and 1804 shown in FIG. 18 can each independently be varied in the same manner as discussed with reference to the spiral waveguide 1402 of FIG. 14, and any desired number of such spirals can be arranged in a desired layout on one or more mutually overlaid layers in an array device. The corresponding fluidic channels can be arranged in corresponding variations, provided that the desired overlapping of evanescent optical fields with adjacent fluidic channels is obtained. Further for example, the optical resonators shown in FIGS. 19 and 20 may be varied in circumference, shape, thickness and numbers as desired. Additional waveguides can be positioned within the microfluidic optical sensors to provide evanescent field interactions with the optical resonators. In an alternative embodiment, the exemplary optical resonator 1904 is sandwiched between fluidic channel regions 1916; and optical resonators 1902 and 1906 are likewise sandwiched. A further embodiment may comprise multiple optical resonators 1904 and/or multiple fluidic channel regions, which may or may not be mutually coextensive and be aligned together in a sandwich.

We claim:
1. A microfluidic optical sensor, comprising:
    an optical waveguide extending between an optical input port and an optical output port, said optical waveguide being capable of propagating light from said optical input port to said optical output port, said optical waveguide comprising an optical waveguide interaction region that comprises an optical waveguide loop;

a fluidic channel extending between a fluid input port and a fluid output port, said fluidic channel being capable of conducting a fluid from said fluid input port to said fluid output port, said fluidic channel comprising a fluidic channel region;

said fluidic channel region being aligned in a sandwich with said optical waveguide interaction region and separated from said optical waveguide interaction region by an interposed spacing material having a thickness;

said thickness being configured to enable transmission of an evanescent field of light through said spacing material between said optical waveguide interaction region and said fluidic channel region.

2. The microfluidic optical sensor of claim 1, in which said fluidic channel region and said optical waveguide interaction region are substantially mutually parallel over a distance.

3. The microfluidic optical sensor of claim 1, in which said fluidic channel region has a first width dimension transverse to a direction of flow of a fluid from said fluid input port to said fluid output port, and in which said optical waveguide interaction region has a second width dimension transverse to a direction of propagation of light from said optical input port to said optical output port, said first width dimension being at least about as large as said second width dimension.

4. The microfluidic optical sensor of claim 3, in which said first width dimension is greater than said second width dimension.

5. The microfluidic optical sensor of claim 1, comprising a second fluidic channel extending between a second fluid input port and a second fluid output port, said second fluidic channel being capable of conducting a fluid from said second fluid input port to said second fluid output port, said second fluidic channel comprising a second fluidic channel region, said second fluidic channel region being aligned in a sandwich with said optical waveguide interaction region and separated from said optical waveguide interaction region by an interposed second spacing material having a second thickness configured to enable transmission of an evanescent field of light through said second spacing material between said optical waveguide interaction region and said second fluidic channel region.

6. The microfluidic optical sensor of claim 1, comprising an optical waveguide interaction region comprising a plurality of optical waveguide loops which are mutually nested to form a spiral having a circumference formed by an outermost optical waveguide loop.

7. The microfluidic optical sensor of claim 1, in which said fluidic channel region has a width dimension transverse to a direction of flow of a fluid from said fluid input port to said fluid output port, said width dimension being at least about as large as a circumference formed by an outermost optical waveguide loop.

8. The microfluidic optical sensor of claim 7, in which said width dimension is greater than said circumference.

9. The microfluidic optical sensor of claim 1, comprising a plurality of fluidic channel regions of said fluidic channel separated from a respective plurality of optical waveguide interaction regions by interposed spacing layers.

10. The microfluidic optical sensor of claim 1, further comprising a second optical waveguide extending between a second optical input port and a second optical output port, said second optical waveguide being capable of propagating light from said second optical input port to said second optical output port, said second optical waveguide comprising a second optical waveguide interaction region that comprises a second optical waveguide loop.

11. A microfluidic optical sensor, comprising:
an optical waveguide extending between an optical input port and an optical output port, said optical waveguide being capable of propagating light from said optical input port to said optical output port;

a fluidic channel extending between a fluid input port and a fluid output port, said fluidic channel being capable of conducting a fluid from said fluid input port to said fluid output port;

an optical resonator separated from said optical waveguide by a first spacing material having a first thickness between the optical resonator and the optical waveguide;

said first thickness being configured to enable transmission of an evanescent field of light through the first spacing material between said optical waveguide and said optical resonator;

said fluidic channel comprising a fluidic cavity region separated from said optical resonator by a second spacing material having a second thickness between the fluidic cavity region and the optical resonator;

said second thickness being configured to enable transmission of an evanescent field of light through the second spacing material between said optical resonator and said fluidic cavity region.

12. The microfluidic optical sensor of claim 11, comprising a plurality of optical resonators.

13. The microfluidic optical sensor of claim 11, where the optical resonator includes a perimeter configured to cause multiple reflections of light.

14. The microfluidic optical sensor of claim 11, in which:
said optical resonator comprises a first circumference;
said fluidic channel region comprises a second circumference; and
said second circumference is at least about as large as said first circumference.

15. The microfluidic optical sensor of claim 11, further comprising a second fluidic channel extending between a second fluid input port and a second fluid output port, said second fluidic channel being capable of conducting a fluid from said second fluid input port to said second fluid output port, said second fluidic channel comprising a second fluidic cavity region separated from said optical resonator by a third spacing material having a third thickness between said second fluidic cavity region and said optical resonator, said third thickness enabling transmission of an evanescent field of light through said third spacing material between said optical resonator and said second fluidic cavity region.

16. A method of making a microfluidic optical sensor, comprising the steps of:
forming an optical waveguide extending between an optical input port and an optical output port, said optical waveguide being capable of propagating light from said optical input port to said optical output port, said optical waveguide comprising an optical waveguide interaction region that comprises an optical waveguide loop;

forming a fluidic channel extending between a fluid input port and a fluid output port, said fluidic channel being capable of conducting a fluid from said fluid input port to said fluid output port, said fluidic channel comprising a fluidic channel region;

wherein said fluidic channel region and said optical waveguide interaction region are aligned in a sandwich and a spacing material, having a thickness, is interposed between said fluidic channel region and said optical waveguide interaction region; and wherein said thickness is configured to enable transmission of an evanescent field of light through said spacing material between said optical waveguide interaction region and said fluidic channel region.

17. The method of claim 16, comprising the steps of:

forming a fluidic channel region having a first width dimension transverse to a direction of flow of a fluid from said fluid input port to said fluid output port;

wherein the optical waveguide interaction region has a second width dimension transverse to a direction of propagation of light from said optical input port to said optical output port, said first width dimension being at least about as large as said second width dimension.

18. The method of claim 16, wherein forming an optical waveguide includes forming an optical waveguide interaction region comprising a plurality of optical waveguide loops which are mutually nested to form a spiral having a circumference formed by an outermost optical waveguide loop.

19. A method of making a microfluidic optical sensor, comprising the steps of:

forming an optical waveguide extending between an optical input port and an optical output port, said optical waveguide being capable of propagating light from said optical input port to said optical output port;

forming a fluidic channel extending between a fluid input port and a fluid output port, said fluidic channel being capable of conducting a fluid from said fluid input port to said fluid output port, said fluidic channel comprising a fluidic cavity region;

forming an optical resonator separated from said optical waveguide by a first spacing material having a first thickness between the optical resonator and the optical waveguide;

wherein said first thickness enables transmission of an evanescent field of light through the first spacing material between said optical waveguide and said optical resonator;

wherein a second spacing material having a second thickness separates said fluidic cavity region and said optical resonator, said second thickness enabling transmission of an evanescent field of light through the second spacing material between said optical resonator and said fluidic cavity region.

20. The method of claim 19 wherein forming an optical resonator includes forming an optical resonator that comprises a first circumference; and wherein forming a fluidic channel includes forming a fluidic channel region that comprises a second circumference; said second circumference being at least about as large as said first circumference.

21. The method of claim 19, further comprising the steps of:

forming a plurality of optical resonators, said plurality of optical resonators being separated from said optical waveguide by a first spacing material having a first thickness between the optical resonators and the optical waveguide, said first thickness enabling transmission of an evanescent field of light through the first spacing material between said optical waveguide and said optical resonators; and wherein a second spacing material having a second thickness separates said fluidic cavity region and said optical resonator, said second thickness enabling transmission of an evanescent field of light through the second spacing material between said optical resonators and said fluidic cavity region.

* * * * *